United States Patent
Hartlep et al.

(10) Patent No.: US 9,101,282 B2
(45) Date of Patent: Aug. 11, 2015

(54) BRAIN TISSUE CLASSIFICATION

(75) Inventors: Andreas Hartlep, Naring (DE);
Christoph Pedain, Munich (DE);
Martin Brady, Phoenix, MD (US);
Raghu Raghavan, Baltimore, MD (US)

(73) Assignee: Brainlab AG, Feldkirchen (DE)

( * ) Notice: Subject to any disclaimer, the term of this patent is extended or adjusted under 35 U.S.C. 154(b) by 1660 days.

(21) Appl. No.: 11/534,383

(22) Filed: Sep. 22, 2006

(65) Prior Publication Data

US 2007/0167788 A1    Jul. 19, 2007

Related U.S. Application Data

(60) Provisional application No. 60/724,231, filed on Oct. 6, 2005.

(30) Foreign Application Priority Data

Sep. 22, 2005  (EP) .................................... 05020672

(51) Int. Cl.
A61B 5/055   (2006.01)
G01R 33/56   (2006.01)
A61B 5/00    (2006.01)
G06T 7/00    (2006.01)

(52) U.S. Cl.
CPC .............. *A61B 5/055* (2013.01); *A61B 5/0042* (2013.01); *A61B 5/4064* (2013.01); *A61B 5/7264* (2013.01);
(Continued)

(58) Field of Classification Search
CPC .... A61B 5/055; A61B 5/4064; A61B 5/0042; A61B 5/7264; A61B 2576/026; G06T 2207/10088; G06T 7/0081; G06T 7/0079; G06T 7/0083; G06T 7/0085; G01R 33/5608

USPC .................. 600/407, 410; 382/128, 170, 173
See application file for complete search history.

(56) References Cited

U.S. PATENT DOCUMENTS 5,361,763 A * 11/1994 Kao et al. ...................... 600/410
6,751,495 B2 * 6/2004 Maier et al. .................. 600/410
(Continued)

FOREIGN PATENT DOCUMENTS

EP          1253557       10/2002

OTHER PUBLICATIONS

Han et al., "Cortical Surface Reconstruction Using a Topology Preserving Geometric Deformable Model", IEEE Workshop on Mathematical Methods in Biomecial Image Analysis, 2001, pp. 213-220.*

(Continued)

*Primary Examiner* — Katherine Fernandez
(74) *Attorney, Agent, or Firm* — Tucker Ellis LLP

(57) ABSTRACT

A medical imaging processing method includes: using an imaging method to acquire at least first and second data sets of a region of interest of a patient's body, with at least one image acquisition parameter being changed so that first and second data sets yield different contrast levels relating to different substance and/or tissue types, and wherein the at least one acquisition parameter used to obtain the first data set is selected to enhance the contrast between one of the substance and/or tissue types relative to other substance and/or tissue types, and the at least one acquisition parameter used to obtain the second data set is selected to enhance the contrast between a different one of the substance and/or tissue types relative other substance and/or tissue types, thereby to optimize the contrast between at least three different substance and/or tissue types; and processing the two data sets to identify the different tissue types and/or boundaries therebetween.

25 Claims, 4 Drawing Sheets

(52) U.S. Cl.
CPC ....... *A61B 2576/026* (2013.01); *G01R 33/5608* (2013.01); *G06T 7/0079* (2013.01); *G06T 7/0081* (2013.01); *G06T 7/0083* (2013.01); *G06T 7/0085* (2013.01); *G06T 2207/10088* (2013.01)

(56) References Cited

U.S. PATENT DOCUMENTS

| | | | | |
|---|---|---|---|---|
| 6,895,107 | B2* | 5/2005 | Park et al. | 382/133 |
| 7,260,248 | B2* | 8/2007 | Kaufman et al. | 382/128 |
| 7,636,461 | B2* | 12/2009 | Spies et al. | 382/128 |
| 2005/0256393 | A1* | 11/2005 | Deoni et al. | 600/410 |

OTHER PUBLICATIONS

Studholme et al., "Accurate Template-Based Correction of Brain MRI Intensity Distortion with Application to Dementia and Aging", IEEE Transactions on Medical Imaging, vol. 23, No. 1, Jan. 2004, pp. 99-110.*

Sled et al., "Understanding intensity non-uniformity in MRI", Proc. MICCAI, 1998, pp. 614-622.*

Wagenknecht et al., "MRI-Based Individual 3D Region-of-Interest Atlases of the Human Brain", Methods Inf. Med., 2004, pp. 383-390.*

Valeria Mongioj, Ph.D. et al.; "Accuracy Evaluation of Fusion of CT, MR, and SPECT Images Using Commercially Available Software Packages"; Int. J. Radiation Oncology Biol. Phys.; vol. 43, No. 1; pp. 227-234, 1998; XP-002366788.

Calvin R. Maurer, Jr., et al.; "A Review of Medical Image Registration"; Interactive Image-Guided Neurosurgery, American Association of Neurological Surgeons; pp. 17-44; 1993; XP-002366700.

Abstracts, XVI International Congress of Head and Neck Radiology, Joint International Conference and Symposium; Frankfurt/Main, Germany; Sep. 4-6, 2003; XP-002366719.

* cited by examiner

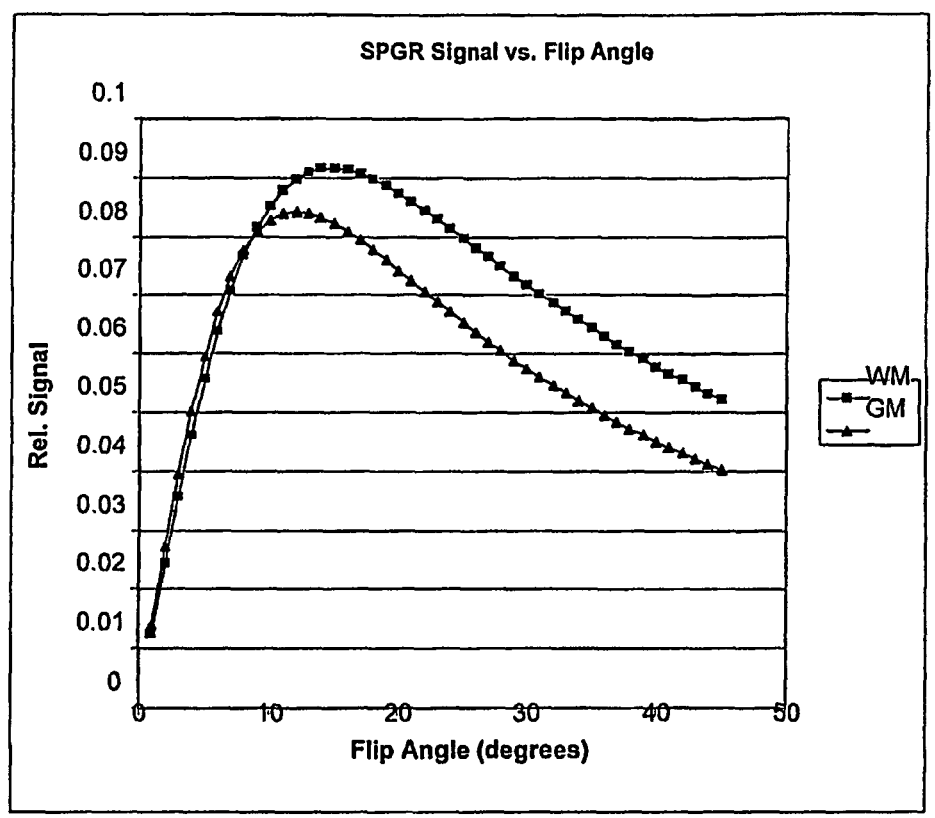
Figure 1. Relative signal strength vs. flip angle for ideal SPGR at TR=20ms for white matter (T1=600ms) and gray matter (T1=900ms).

SPGR – Flip 25°

SPGR – Flip 7°

Ratio

BRAIN TISSUE CLASSIFICATION

RELATED APPLICATION DATA

This application claims priority of U.S. Provisional Application No. 60/724,231 filed on Oct. 6, 2005, which is incorporated herein by reference in its entirety.

FIELD OF THE INVENTION

The present invention relates to image processing for surface delineation and, more particularly, to a method and apparatus for detecting boundaries between brain tissue and cerebrospinal fluid (CSF) filled regions to classify brain tissue.

BACKGROUND OF THE INVENTION

Tissue-CSF boundaries between brain tissue and cerebrospinal fluid (CSF) occur primarily at an outer cortical surface and in interior regions of the brain at CSF-filled ventricles. Locating these surfaces is beneficial for some neurosurgical procedures, such as convection-enhanced drug delivery, since placement of infusion catheters too close to CSF boundaries is known to lead to poor dispersion of infusate in tissue, as the infusate flows into the less-resistive CSF-filled regions.

Large CSF-filled structures are easily distinguished from brain tissue in many MRI imaging sequences. At the cortical surface, however, thin sulci are often narrower than the resolution provided by MR imagery and, thus, are not reliably detected. Furthermore, the problem can be complicated by brain pathologies. In particular, edema in white matter can greatly alter signal levels, making it difficult to separate white matter from other tissues.

In order to overcome this limitation, conventional methods detect the thicker cortical gray matter, and then use topological knowledge to estimate a location of an outer surface of the detected gray matter. The problem is thus transformed into finding a reliable segmentation of the cortical gray matter.

The cortex generally has a consistent thickness of about 3 mm. However, it can be difficult to differentiate gray matter from white matter. This difficulty is often compounded by inhomogeneities in the RF fields, making it difficult or impossible to separate gray and white matter with a constant threshold value.

A common approach to tissue classification is to assign a label to each voxel, identifying it as white matter (WM), grey matter (GM), or CSF, based on the voxel's signal level. Threshold levels separating the tissues, for example, can be obtained from user input or estimated from the image histogram. Other methods may use different representations in an attempt to more accurately identify surfaces that separate the three categories. Deformable surface models describe the interface either as a parameterized mesh of triangles (see, e.g., M. Kass, A. Witkin, and D. Terzopoulos, "Snakes: Active Contour Models," Intl. J. Comp. Vision, v. 1, pp. 312-333, 1988), or using level set methods, where a zero level set implicitly defines the boundary (X. Zeng, L. H. Staib, R. T. Shultz, and J. S. Duncan, "Segmentation and Measurement of the Cortex from 3D MR Images Using Coupled Surfaces Propagation," IEEE Trans. Med. Imaging, v. 18, pp. 100-111, 1999). Deformable surface models can represent partial voxels, but are generally complicated to implement and computationally intensive to run.

Brain tissue classification methods that use MRI data as input can encounter difficulties. These difficulties include a variation in signal response, and structures that are smaller than the sampling rate. These issues are described below.

MRI data used for brain tissue classification often contain some amount of artifact or distortion due to inhomogeneities in the radio frequency (RF) fields and magnetic susceptibility variations in the tissue being imaged. These effects give rise to small variations in the signal intensity that depend on the position of the sample location. These types of distortions are usually modeled as a multiplicative slowly-varying 'gain' field that modifies the expected signal values, e.g., $M(x, y, z)=G(x, y, z) \times I(x, y, z)$, where M denotes the measured signal, I is the undistorted signal, G represents the gain field, and "x" denotes an element-wise product. G is a low frequency field with values near unity. The intensity normalization step attempts to estimate the gain field and use it to restore the undistorted image.

A simple filtering method is often used to estimate G. A three-dimensional low-pass filter with a wide window can be applied to the image. Mean, median, and Gaussian filters have been used for this purpose. The low-pass result can be used to estimate the gain field.

The normalization problem is sometimes converted into the estimation of an additive 'bias' field $B=\log(G)$ by taking the logarithm of the expression. W. M. Wells, W. E. Grimson, R. Kikinis, F. A. Jolesz, "Adaptive Segmentation of MRI Data," IEEE Trans. Med. Imaging, v. 15, pp. 429-442, 1996 suggested this approach, and an expectation maximization approach to solve the problem. In this method, normalization and tissue classification are combined. A statistical classification is performed, followed by bias field estimation using the classification results, and then the estimated bias is removed. These steps are iterated to converge on a normalized classification. Many variations of this strategy have been proposed. The difficulties with this method are that they are complicated to implement and relatively time-consuming to perform.

The second difficulty, structures too small to be detected at MRI resolution, occurs frequently at the cortical surface. Sufficiently large CSF-filled structures in the brain are usually easy to distinguish by their signal level alone. But the outer surface of the cortex, a GM-CSF boundary, has a complex geometry in which the CSF regions can be obscured. The topology is that of a highly folded sheet of gray matter about three millimeters thick. The CSF-filled space between the inner folds (sulci) may be very thin relative to the MRI resolution and thus may not always directly visible in typical MRI data. A sulcus may appear in MRI as a continuous region of gray matter.

Knowledge of the brain's topology is often used in cortical surface finding algorithms in order to locate thin sulci that are not directly visible. The inner cortical GM-WM boundary is more easily located, as the white matter structures inside the gyri are usually thick enough to be detected. Therefore, one can locate the cortical GM-WM boundary, and then use this information to help locate the GM-CSF boundary. X. Zeng, L. H. Staib, R. T. Shultz, and J. S. Duncan, "Segmentation and Measurement of the Cortex from 3D MR Images Using Coupled Surfaces Propagation," IEEE Trans. Med. Imaging, v. 18, pp. 100-111, 1999, developed a level set method for segmenting the cortex that simultaneously evolves a pair of surfaces, one seeking the WM-GM cortical boundary and the other seeking the outer GM-CSF cortical surface. An additional constraint forces the two implicit surfaces to remain about three millimeters apart.

The coupled boundary level set approach has difficulty representing a pair of GM-CSF boundaries that are separated by less than the voxel resolution. X. Han, C. Xu, D. Tosun, and J. Prince, "Cortical Surface Reconstruction Using a Topology Preserving Geometric Deformable Model," 5th IEEE Workshop on Math. Methods in Bio. Image Anal., Kauai, Hi., pp. 213-220, December 2001 propose a modified topology-preserving level set method to find the WM-GM cortical boundary only. They then compute the 'skeleton' of the cortical gray matter, which locates regions that are maximally distant from the WM-GM boundary on the GM side. This method locates the central plane within sulci well. The skeleton regions are then marked as cortical surface. This method performs well at locating the cortical surface, but the level set approach for locating the GM-WM boundary is compute-intensive, considering that the WM-GM interface is amenable to simpler classification methods, such as thresholding.

SUMMARY OF THE INVENTION

The present invention provides a medical image processing system and method for classifying, preferably automatically, major tissue types, such as white matter (WM), gray matter (GM) and cerebro-spinal fluid (CSF). In a preferred embodiment, the system and method, data from two or more similar volume data sets is used, the volume data sets being similar except that at least one acquisition parameter has been varied to obtain different tissue contrast in the different volume data sets. The volume data sets preferably are generated by magnetic resonance imaging (MRI), contrast is improved and/or inhomogeneities are reduced by combining the two similar, yet parameter varied, data sets, as by taking a ratio of the data sets. The selection of acquisition parameters and combining methodologies are herein described.

The classification method may be further optimized by adjusting the volume signal levels so that the classification boundaries tend to lie on edges in the original image.

As discussed herein, CSF boundaries in brain tissue can be identified from medical images which, for example, can be used to identify edema. The preferred imaging modality is magnetic resonance imaging, but any modality with sufficient WM/GM/CSF contrast and resolution fine enough to represent the cortex (a few millimeters) will suffice for use in classifying different brain tissues and identifying boundaries. Voxels that primarily contain CSF (within the ventricles, surgical resection cavities, and some sulci) may be identified, and voxels containing the cortical surface, even when the voxel's volume primarily contains gray matter (thin sulci), may be identified.

RF inhomogeneities can be minimized by using at least two related image sequences in order to estimate and remove a bias term arising from the inhomogeneity. Multiple imaging modalities can be employed in order to identify white matter, even in the presence of pathological conditions. MR diffusion tensor imaging may be used, as it is particularly sensitive to variations in cell topology and is thus preferred for this task.

Preferably, medical images are used that show contrast between the white matter, gray matter, and CSF. In previous methods, this usually is taken to be a single three-dimensional MRI volume. Advantage is gained by using two similar MRI volumes with preferably only a single, but optionally two or more varied acquisition parameters to obtain different WM/GM/CSF contrast levels. It may be assumed that the gain field arising from magnetic susceptibility and RF field inhomogeneity will be similar in the two volumes. By taking the ratio of the two volumes, the common gain factor can be eliminated. Furthermore, by carefully selecting the acquisition parameters, the WM/GM/CSF contrast can be increased with respect to the individual volumes. This methodology can improve the performance of the remainder of the overall classifying method, but is not required. Some low-frequency distortion may remain, but it can be addressed through further processing as described below.

In particular, WM, GM and CSF can be classified by thresholding. Remaining low-frequency bias can be detected and normalized in this step also. Iterative normalization and classification algorithms generally look at the sets of values of each type within a region of the volume, and base the gain estimation on these sets; see W. M. Wells, W. E. Grimson, R. Kikinis, F. A. Jolesz, "Adaptive Segmentation of MRI Data," IEEE Trans. Med. Imaging, v. 15, pp. 429-442, 1996. Because the entire set of voxels is used in this procedure, such procedure can be complicated and time-consuming. Thus, it is preferred to define the current threshold and normalization by looking only at the WM/GM/CSF boundaries, and a gain correction may be selected that tends to place the boundaries over edges in the image.

Thin sulcal CSF boundaries are often too narrow to be directly detected in any common MR sequence. As described herein, cortical gray matter may be detected (which is much more robust) and then a 'skeletonizing' algorithm can be used to locate the thin sulcal boundaries centered in a fold of cortical gray matter, similar to X. Han, C. Xu, D. Tosun, and J. Prince, "Cortical Surface Reconstruction Using a Topology Preserving Geometric Deformable Model," 5th IEEE Workshop on Math. Methods in Bio. Image Anal., Kauai, Hi., pp. 213-220, December 2001. Thicker areas of CSF will not be completely covered by the skeleton, but these are usually detected in the previous step by thresholding, since thick CSF usually is easy to distinguish.

BRIEF DESCRIPTION OF THE DRAWINGS

The forgoing and other embodiments of the invention are hereinafter discussed with reference to the drawings.

FIG. 1 is a graph showing relative signal strength vs. flip angle for ideal SPGR at TR=20 ms for white matter and gray matter.

DETAILED DESCRIPTION

A CSF boundary detection procedure includes the steps shown below.
1. Image pair pre-processing to enhance contrast and reduce bias (optional).
2. WM/GM/CSF thresholded classification/inhomogeneity correction.
3. Thin sulcus detection using the gray matter skeleton.

1. Image Pair Pre-Processing

Two MRI volumes can be acquired using identical acquisition parameters, varying, for example, one acquisition parameter. These two volumes can be co-registered, if necessary, using known methods. Then the ratio of the two volumes is determined (any division by zero is replaced with the value zero). The ratio, for example, may be based on a voxel by voxel or data point by data point calculation. Determining the ratio of the two volumes has two advantages. First, intensity variations due to field inhomogeneities tend to be similar in both images, so the division tends to normalize this undesirable effect such that it is insignificant. Second, when the acquisition parameters are chosen correctly, the GM/WM separation can be enhanced compared to a single MR acquisition.

The preferred MRI sequence for brain tissue classification is a 3D Spoiled Gradient Recalled Echo (SPGR). The signal can be modeled by Equation 1 (ignoring noise and inhomogeneity):

$$S=K*PD*(1-e^{-TR/T1})\sin(FA)/(1-(\cos(FA)e^{-TR/T1})) \quad \text{Equation 1}$$

where T1 and PD depend upon the tissue properties, while the repetition time (TR) and flip angle (FA) are controlled parameters of the acquisition. Variable K incorporates several constant factors, including functions of the echo time (TE) and the tissue T2. In the SPGR volumes, the tissue T1 and proton density (PD) both contribute significantly to the signal levels. For flip angles above the Ernst angle (angle that maximizes the signal), the lower T1 of white matter typically accounts for a 30-40% elevation of the white matter signal relative to gray matter. However, the PD of white matter is about 88% of gray matter, so the relative WM signal is about 14-23% higher than GM. Below the Ernst angle, images are PD-weighted, and relatively insensitive to WM/GM T1 variations. This can be seen in the graph of FIG. 1.

In this method, two SPGR volumes are acquired: A, with a flip angle above the Ernst angle, and B, with a flip angle below the Ernst angle for the range of T1 of WM and GM tissues. Then the ratio of the two volumes, A/B can be computed. In this volume, the PD weighting may be removed, and the signal variation between WM and GM is due mainly to the T1 differences, e.g., 30-40%.

Figure 2A:
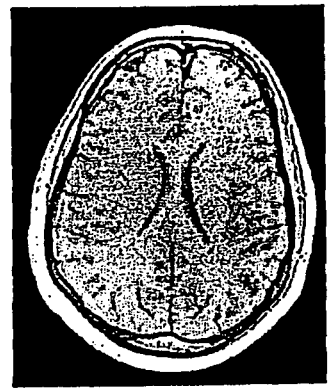
FIG. 2A-2C are SPRG slices of a brain.
Figure 2B:
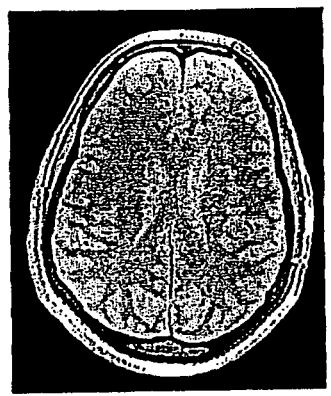
Figure 2C:
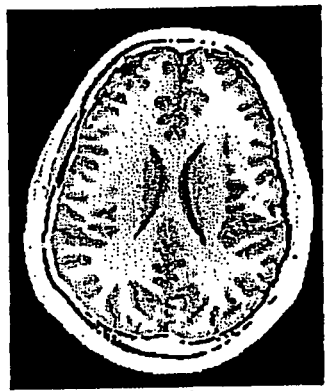

FIGS. 2A-2C compare a slice of the low flip angle SPGR, the high flip angle SPGR, and their ratio. The ratio displays a strong separation between white and gray matter, and the CSF, where thick enough, also is separated from the gray value. The typical intensity inhomogeneity is easy to observe in the 25 degree flip angle image of FIG. 2A, in which the intensities are skewed lower in the middle of the image and brighter near the outer edges.

Gray-white contrast enhancement can be obtained using spin echo based T1-weighted sequences also, by varying the repetition time, TR, to modify the T1-weighting. Spin echo signal response is generally modeled as Equation 2:

$$S=K*PD*(1-e^{-TR/T1}) \quad \text{Equation 2}$$

again lumping all of the constant factors into K. By selecting one TR near the tissue T1, and a second TR several times larger than the average T1, we obtain T1-weighted and PD weighted volumes with response similar to that shown in FIG. 2. Their ratio gives a similarly enhanced gray-white contrast. Spin-echo sequences are far less prone to the inhomogeneities inherent in SPGR. However, if acquired using surface coils, the variability in the coil's RF reception can produce significant low frequency variations that are normalized by this method.

2. WM/GM/CSF Thresholded Classification/Inhomogeneity Correction

The gray/white threshold can be set by asking a user to select a set of sample points in a user interface, e.g., to 'paint' a region by modeling a set of values underlying the selected gray or white matter region as a Gaussian distribution, it is easy to extract a mean and standard deviation for that region. This input should be accepted for WM, GM, and CSF. From white and gray values, a WM-GM threshold can be calculated as the point at which the two Gaussian distribution curves intersect (e.g., the value at which a point is equally likely to be white or gray matter). A GM-CSF threshold can be computed in the same manner.

The initial threshold value can be a first approximation to the optimal threshold value, but it may not be ideal. Furthermore, even after normalization, there may be some remaining variation in WM/GM/CSF mean intensities across the image.

A low frequency gain field G can be estimated to correct these variations. The gain volume can be at a much coarser resolution than the image. Approximately 1 cm resolution is appropriate for G, about a factor of ten coarser than the image volume.

Prior methods estimate the gain from the thresholded image by looking at the statistics of the sets of voxels in each of the three categories; see W. M. Wells, W. E. Grimson, R. Kikinis, F. A. Jolesz, "Adaptive Segmentation of MRI Data," IEEE Trans. Med. Imaging, v. 15, pp. 429-442, 1996. Gain adjustments that center the statistics of local sub-regions towards the global value are specified. As described herein, and in contrast to the prior art, focus may be placed on the alignment of the boundaries between the sub-regions. The boundaries in the original volume can be detected by any standard three-dimensional edge detection operation. In the preferred implementation, the magnitude of the gradient of the image volume can be computed. A classification volume can be formed by assigning integers 0, 1, 2 to CSF, GM, and WM regions determined by thresholding. An edge detection of the classification volume then can be computed. A measure of the quality of the match of the boundaries of the image and classification volumes then can be defined. The mutual information measure is well suited for this purpose (see P. Viola and W. M. Wells III, "Alignment by Maximization of Mutual Information," in Intl. Conf. on Comp. Vision, E. Grimson, S. Shafer, A. Blake, and K. Sugihara, Eds., IEEE Computer Society Press, Los Alamitos, Calif., pp. 16-23, 1995 for the computation of the mutual information for volume registration). Simpler measures are also acceptable, such as a normalized sum of the product of the two volumes, as shown in Equation 3:

$$\frac{\sum_{x,y,z} i_{x,y,z} \cdot c_{x,y,z}}{\sum_{x,y,z} c_{x,y,z}} \quad \text{Equation 3}$$

Symbol i denotes the value of voxel position (x, y, z) of the edge-detected image volume, normalized by the current gain, and c denotes the value of the edge-detected classification volume.

The gain field can be adjusted to maximize the mutual information or other similarity measure. Gradient descent is suitable for this optimization procedure, since the starting point is generally close to the optimal. Furthermore, the change in the measure can be computed far more rapidly than the measure itself, since the effect of one gain field voxel is limited to a small sub-volume of the image field.

3. Thin Sulcus Detection

Classification will adequately identify the WM/GM/CSF regions that are large relative to the image resolution. The method proposed by X. Han, C. Xu, D. Tosun, and J. Prince, "Cortical Surface Reconstruction Using a Topology Preserving Geometric Deformable Model," 5th IEEE Workshop on Math. Methods in Bio. Image Anal., Kauai, Hi., pp. 213-220, December 2001, can be used at this step to locate cortical surfaces in thin sulci using a skeleton computation. The GM skeleton is the set of points of maximal distance from the WM-GM boundary, which tends to be precisely the location of a thin cortical surface in the sulcal fold of cortical gray.

First, a signed distance map from the WM-GM boundary can be computed. The Laplacian of the distance map can be computed, and Laplacian values above a fixed threshold can be classified as cortical surface.

The method may lack the sub-pixel accuracy of the level set approach, but is simpler and faster. Preferably all CSF-containing voxels are marked, and the sub-pixel accuracy is unnecessary in this application. A refinement to this method is to limit the maximum distance that the skeleton is allowed to traverse. If it is assumed that the cortical GM-CSF surface is always within some maximum distance (several millimeters) of the cortical WM-GM boundary, then points at greater distance are not considered. This eliminates many false positive skeleton values from deep brain gray matter structures.

Figure 3:
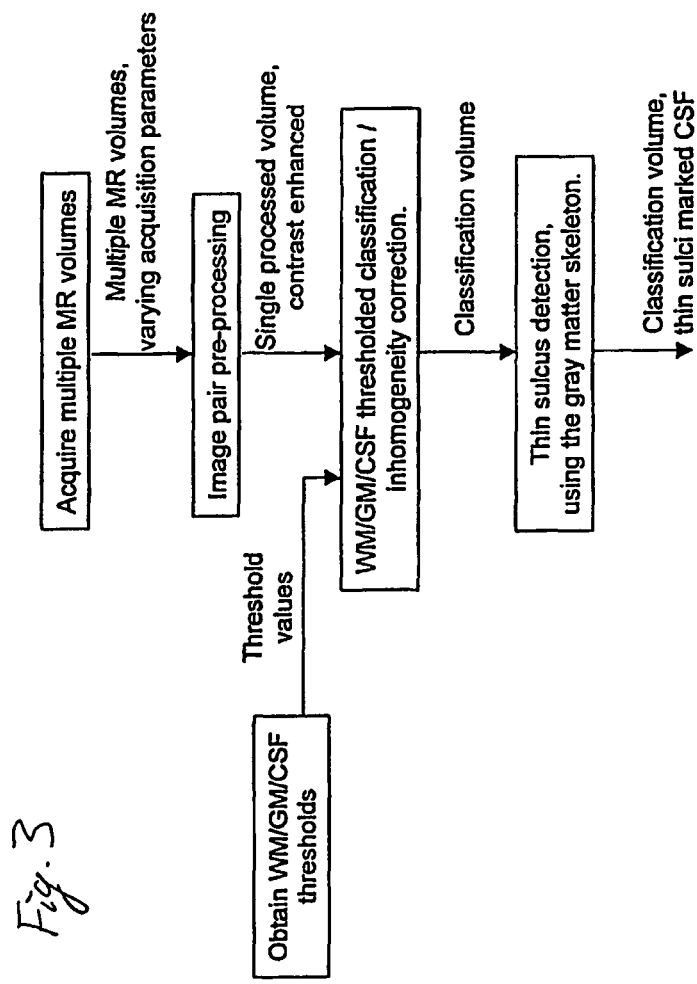
FIG. 3 is a flow chart showing the steps of an exemplary method in accordance with the invention.

FIG. 3 shows the steps of an exemplary method in accordance with the invention.

Different imaging modalities have different advantages and disadvantages. For example, images acquired with MRI (Magnetic Resonance Imaging) grey and white matter of brain tissue can easily be distinguished, but spatial resolution and spatial accuracy is worse compared to images acquired with CT (Computer Tomography). It is quite difficult, however, to distinguish between grey and white matter in CT images.

Usually in T1-weighted (T1w) MR images a sufficient spatial resolution can be reached, but water, especially edema, can hardly be seen. T2-weighted (T2w) images can be used to identify regions of CNF (Cerebro-Spinal Fluid). A very sufficient imaging dataset to identify edema can be calculated from diffusion weighted (DWI) MR images or from the diffusion tensor (DTI) using the fact that the anisotropy in the movement of water molecules will decrease in edema regions. However, DWI images currently suffer from a low spatial resolution and accuracy.

For a highly reliable segmentation of brain surfaces, the advantages from the various imaging modalities can be combined. For example, if T1w and T2w data sets are morphed and fused to the CT data, the T2w dataset can be used for detection of outer surfaces and the T1w dataset can be used to distinguish between white and grey matter. From those datasets a new dataset (DS1) can be created showing the boundaries between CSF and white and grey matter. If the DWI dataset is fused and morphed to the CT dataset, a new (DWI1) dataset is created showing diffusion related data in an anatomical correct environment. DWI1 can be used to identify edema. This information can be fused to DS1 creating a new dataset DS2 that contains anatomically correct information about boundaries between grey and white matter, brain surfaces and edema. In the same manner more datasets containing more information can be used to identify more required regions.

Furthermore, datasets can be used to correct for image inhomogenieties or other imaging errors. For example, distortions from phase errors can be corrected using field maps, and the corrected images can be used to correct the other data sets.

Figure 4:
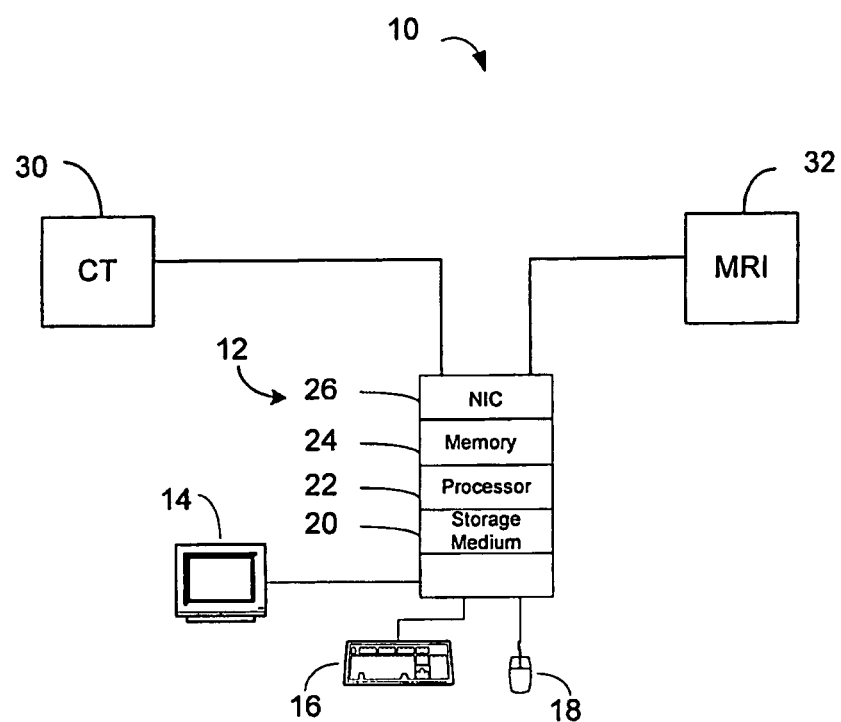
FIG. 4 is an exemplary device which can be used in performing a method in accordance with the invention.

FIG. 4 is a block diagram of a system 10 for implementing one or more of the methods described herein. The system 10 includes a computer 12 for processing data, and a display 14 for viewing system information. A keyboard 16 and pointing device 18 may be used for data entry, data display, screen navigation, etc. The keyboard 16 and pointing device 18 may be separate from the computer 12 or they may be integral to it. A computer mouse or other device that points to or otherwise identifies a location, action, etc., e.g., by a point and click method or some other method, are examples of a pointing device. Alternatively, a touch screen (not shown) may be used in place of the keyboard 16 and pointing device 18. A touch screen is well known by those skilled in the art and will not be described herein.

Included in the computer 12 is a storage medium 20 for storing information, such as application data, screen information, programs, etc. The storage medium 20 may be a hard drive, for example. A processor 22, such as an AMD Athlon 64® processor or an Intel Pentium IV® processor, combined with a memory 24 and the storage medium 20 execute programs to perform various functions, such as data entry, numerical calculations, screen display, system setup, etc. A network interface card (NIC) 26 allows the computer 22 to communicate with devices external to the system 10.

Communicatively coupled to the computer 12 is a first imaging system 30 (e.g., a CT imaging system) and a second imaging system 32b (e.g., an MRI system). As will be appreciated, other imaging systems may be utilized in place of the CT and MRI systems. The first and second imaging systems can provide imaging data to the computer 12, which uses the data in accordance with the method described herein.

The actual code for performing the functions described herein can be readily programmed by a person having ordinary skill in the art of computer programming in any of a number of conventional programming languages based on the disclosure herein. Consequently, further detail as to the particular code itself has been omitted for sake of brevity.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A computer-implemented medical imaging processing method comprising executing, on a processor of a computer, steps of:

acquiring, at the processor, at least first and second data sets of a region of interest of a patient's body by imaging the patient's body, with at least one image acquisition parameter being changed, by the processor, so that the first and second data sets yield different contrast levels relating to different tissue types, and with at least one image acquisition parameter used to obtain the first data set being selected, by the processor, to enhance the contrast between one of the tissue types relative to other tissue types, and with the at least one image acquisition parameter used to obtain the second data set being selected, by the processor, to enhance the contrast between a different one of the tissue types relative other tissue types, thereby to optimize the contrast between at least three different tissue types;

processing, by the processor, at least the first and second data sets to identify the different tissue types and/or boundaries therebetween, said processing including: forming, by the processor, a combined data set by combining the at least first and second data sets; and calculating, by the processor, a gain field to correct for variations in mean intensities across the combined data set, wherein the gain field is adjusted, by the processor, to maximize a similarity measure between detected boundaries of sub-regions in the combined data set and detected boundaries of a classification volume derived from the combined data set; and using, by the processor, a skeletonizing algorithm on at least one of the identified tissue types or boundaries to locate sulci.

2. The method according to claim 1, wherein the first and second data sets are obtained by magnetic resonance imaging.

3. The method according to claim 1, wherein a single image acquisition parameter is changed, by the processor, when obtaining the first and second data sets.

4. The method according to claim 3, wherein the single image acquisition parameter is changed, by the processor, so as to enhance T1 contrast.

5. The method according to claim 1, wherein the at least one image acquisition parameter is a flip angle.

6. The method according to claim 5, wherein the flip angle is set above and below the Ernst angle for the first and second data sets, respectively.

7. The method according to claim 1, further comprising varying, by the processor, the at least one image acquisition parameter to optimize the data acquisition with respect to the distinction of white matter and grey matter in a first data set.

8. The method according to claim 1, further comprising varying, by the processor, the at least one image acquisition parameter to optimize data acquisition with respect to the distinction of white matter and cerebrospinal fluid filled regions in a second data set.

9. The method according to claim 1, further comprising classifying, by the processor, white matter, gray matter and cerebrospinal fluid filled regions in the classification volume by thresholding.

10. The method according to claim 1, further comprising calculating, by the processor, the boundaries for white mater, grey matter and/or cerebrospinal fluid from the at least first and second data sets.

11. The method according to claim 1, further comprising including, by the processor, assumptions, estimates or a predefined atlas about anatomical structures and/or physiological properties of one or more volume elements in the classification volume based on an assignment using image data.

12. The method according to claim 1, further comprising using, by the processor, a diffusion tensor MRI to acquire the first and/or second data sets.

13. The method according to claim 1, wherein the first and/or second data sets comprise an MRI image with a spatial resolution of at least one by one by three millimeters.

14. The method according to claim 1, wherein the imaging includes using MRI sequences with varying flip angles.

15. The method according to claim 1, wherein using the skeletonizing algorithm includes defining, by the processor, a gray-matter skeleton as a set of points within a predetermined distance from a white matter-gray matter boundary.

16. The method according to claim 1, further comprising adjusting, by the processor, signal levels for the first and second data sets so that boundaries lie on edges in the preprocessed first and second data sets.

17. A computer program embodied on a non-transitory computer-readable medium for computer-implemented medical imaging processing, comprising:

code that directs imaging of a patient's body to acquire, at a processor of a computer, at least first and second data sets of a region of interest of the patient's body, with at least one image acquisition parameter being changed, by the processor, so that first and second data sets yield different contrast levels relating to different tissue types, and wherein the at least one image acquisition parameter used to obtain the first data set is selected, by the processor, to enhance the contrast between one of the tissue types relative to other tissue types, and the at least one image acquisition parameter used to obtain the second data set is selected, by the processor, to enhance the contrast between a different one of the tissue types relative other tissue types, thereby to optimize the contrast between at least three different tissue types;

code for processing, by the processor, the at least first and second data sets to identify the different tissue types and/or boundaries therebetween, said processing including forming, by the processor, a combined data set by combining the at least first and second data sets; and calculating, by the processor, a gain field to correct for variations in mean intensities across the combined data set, wherein the gain field is adjusted, by the processor, to maximize a similarity measure between detected boundaries of sub-regions in the combined data set and detected boundaries of a classification volume derived from the combined data set; and code for implementing, by the processor, a skeletonizing algorithm on at least one of the identified tissue types or boundaries to locate sulci.

18. The computer program according to claim 17, wherein the code for implementing the skeletonizing algorithm includes code for defining, by the processor, a gray-matter skeleton as a set of points within a predetermined distance from a white matter-gray matter boundary.

19. The computer program according to claim 17, further comprising code for adjusting, by the processor, volume signal levels so that boundaries lie on edges in the first and second data sets.

20. An apparatus for medical image processing, comprising:

at least one imaging or data acquisition system;

a processor and memory; and image acquisition and processing logic stored in the memory and executable by the processor, wherein the image acquisition and processing logic includes:

logic for directing imaging of a patient's body to acquire, at the processor, at least first and second data sets of a region of interest of the patient's body, with at least one image acquisition parameter being changed, by the processor, so that first and second data sets yield different contrast levels relating to different tissue types, and wherein the at least one image acquisition parameter used to obtain the first data set is selected, by the processor, to enhance the contrast between one of the tissue types relative to other tissue types, and the at least one image acquisition parameter used to obtain the second data set is selected, by the processor, to enhance the contrast between a different one of the tissue types relative other tissue types, thereby to optimize the contrast between at least three different tissue types;

logic for processing, by the processor, the at least first and second data sets to identify the different tissue types and/or boundaries therebetween, said processing including: forming a combined data set by combining the at least first and second data sets; and calculating, by the processor, a gain field to correct for variations in mean intensities across the combined data set, wherein the gain field is adjusted, by the processor, to maximize a similarity measure between detected boundaries of sub-regions in the combined data set and detected boundaries of a classification volume derived from the combined data set; and logic for implementing, by the processor a skeletonizing algorithm on at least one of the identified tissue types or boundaries to locate sulci.

21. The apparatus according to claim 20, wherein the logic for implementing the skeletonizing algorithm includes logic for defining, by the processor, a gray-matter skeleton as a set of points within a predetermined distance from a white matter-gray matter boundary.

22. The apparatus according to claim 20, further comprising logic for adjusting, by the processor, volume signal levels so that boundaries lie on edges in the first and second data sets.

23. A computer-implemented medical imaging processing method comprising executing, on a processor of a computer, steps of:

obtaining, at the processor, at least first and second data sets of a region of interest of a patient's body that have been produced by an imaging method for imaging the patient's body with at least one image acquisition parameter being different such that first and second data sets yield different contrast levels relating to different tissue types, and wherein the at least one image acquisition parameter used to obtain the first data set enhances the contrast between one of the tissue types relative to other tissue types, and the at least one image acquisition parameter used to obtain the second data set enhance the contrast between a different one of the tissue types relative other tissue types;

processing, by the processor, the at least first and second data sets to identify the different tissue types and/or boundaries therebetween, said processing including:
forming, by the processor, a combined data set by combining the at least first and second data sets; and calculating, by the processor, a gain field to correct for variations in mean intensities across the combined data set, wherein the gain field is adjusted, by the processor, to maximize a similarity measure between detected boundaries of sub-regions in the combined data set and detected boundaries of a classification volume derived from the combined data set;

using, by the processor, a skeletonizing algorithm on at least one of the identified tissue types or boundaries to locate sulci; and outputting, by the processor, the location of the sulci for review.

24. The method according to claim 23, wherein using a skeletonizing algorithm includes defining, by the processor, a gray-matter skeleton as a set of points within a predetermined distance from a white matter-gray matter boundary.

25. The method according to claim 23, further comprising adjusting, by the processor, volume signal levels so that boundaries lie on edges in the first and second data sets.

* * * * *